(12) United States Patent
Heim

(10) Patent No.: US 8,540,879 B2
(45) Date of Patent: Sep. 24, 2013

(54) STEAM-STERILIZABLE BLOOD SEPARATING DEVICE

(75) Inventor: Gerd H. Heim, Gladbeck (DE)

(73) Assignee: Hemacon GmbH, Duesseldorf (DE)

( * ) Notice: Subject to any disclaimer, the term of this patent is extended or adjusted under 35 U.S.C. 154(b) by 62 days.

(21) Appl. No.: 11/989,497

(22) PCT Filed: Jul. 26, 2006

(86) PCT No.: PCT/DE2006/001308
§ 371 (c)(1),
(2), (4) Date: Feb. 20, 2008

(87) PCT Pub. No.: WO2007/012321
PCT Pub. Date: Feb. 1, 2007

(65) Prior Publication Data
US 2009/0261038 A1    Oct. 22, 2009

(30) Foreign Application Priority Data
Jul. 26, 2005   (DE) .................. 10 2005 035 528

(51) Int. Cl.
*A61L 2/07* (2006.01)
*B01D 65/02* (2006.01)
*B01D 63/02* (2006.01)

(52) U.S. Cl.
USPC ........ 210/636; 210/233; 210/252; 210/257.1; 210/436; 210/472; 210/500.23; 210/500.41; 422/1; 422/26

(58) Field of Classification Search
USPC .............. 210/636, 233, 252, 257.1, 436, 472, 210/500.23, 500.41; 422/1, 26
See application file for complete search history.

(56) References Cited

U.S. PATENT DOCUMENTS

| | | | | |
|---|---|---|---|---|
| 5,405,343 A | * | 4/1995 | Mohr | ............................ 604/416 |
| 5,587,070 A | * | 12/1996 | Pall et al. | ...................... 210/202 |
| 6,171,493 B1 | * | 1/2001 | Zia et al. | .................... 210/257.1 |
| 6,544,424 B1 | * | 4/2003 | Shevitz | ......................... 210/650 |

(Continued)

FOREIGN PATENT DOCUMENTS

| | | |
|---|---|---|
| DE | 197 33 407 | 2/1999 |
| DE | 200 14 311 | 2/2001 |

(Continued)

OTHER PUBLICATIONS

International Search Report, PCT/DE2006/001308 (Mar. 2007).

(Continued)

*Primary Examiner* — John Kim
(74) *Attorney, Agent, or Firm* — Morgan, Lewis & Bockius LLP

(57) ABSTRACT

A device for separating blood into individual components and/or groups of components, in the form of a sterilizable system includes a filter arrangement forming inlet and outlet chambers using filter elements arranged therein, and respective receptacles for cellular blood components and for blood plasma. The inlet chamber can be connected to the blood source via a line on the inlet side to conduct the blood and is connected, on the outlet side, to the cellular blood components receptacle. The outlet chamber is connected to the blood plasma receptacle via a line on the outlet side. Thermal sterilization is used to sterilize the device by opening a respective line into the inlet-side line of the inlet chamber, into the inlet chamber and the outlet-side line of the outlet chamber, or into the outlet chamber, the line being connected to the exterior via a hydrophobic or hydrophilic filter.

16 Claims, 1 Drawing Sheet

(56) References Cited

U.S. PATENT DOCUMENTS

| | | |
|---|---|---|
| 7,025,881 B2 | 4/2006 | Heim |
| 2002/0183678 A1* | 12/2002 | Heim .......................... 604/6.04 |
| 2005/0051486 A1 | 3/2005 | Zuk, Jr. |
| 2007/0043317 A1 | 2/2007 | Sugawara |

FOREIGN PATENT DOCUMENTS

| | | |
|---|---|---|
| EP | 1 671 664 | 6/2006 |
| RU | 2285543 | 10/2006 |
| RU | 2290956 | 1/2007 |
| WO | WO 2005/032619 | 4/2005 |

OTHER PUBLICATIONS

Office Action dated Mar. 12, 2010 from Chinese Patent Office in Chinese Application No. 200680035304.5 (and English translation thereof).

\* cited by examiner

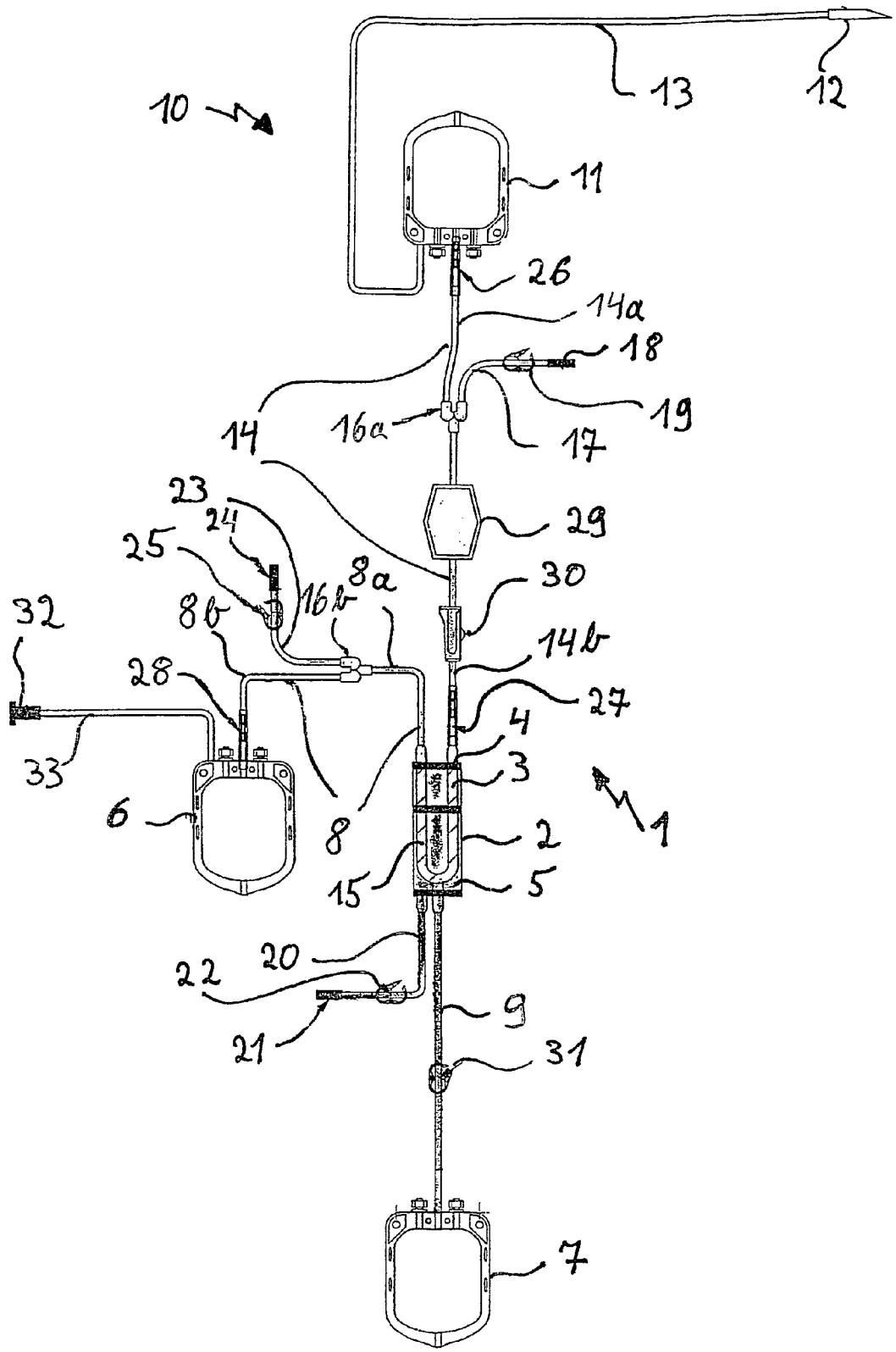

STEAM-STERILIZABLE BLOOD SEPARATING DEVICE

CROSS REFERENCE TO RELATED APPLICATIONS

Applicant claims priority under 35 U.S.C. §119 of German Application No. 10 2005 035 528.5 filed Jul. 26, 2005. Applicant also claims priority under 35 U.S.C. §365 of PCT/DE2006/001308 filed Jul. 26, 2006. The international application under PCT article 21(2) was not published in English.

The invention relates to a device for fractionating blood into single ones and/or groups of its components in the form of a sterilizable system comprising a filter arrangement which, by means of filter elements dispersed therein, forms an inlet chamber and an outlet chamber, and a receptacle for cellular blood components and a receptacle for blood plasma, where the inlet chamber of the filter arrangement can be connected by conduit on the entry side to a blood source and is connected by conduit on the exit side to a receptacle for cellular components of blood, and where the outlet chamber is connected by conduit on the exit side to a receptacle for blood plasma.

The invention further relates to a method for the steam sterilization of a device for fractionating blood into individual ones and/or groups of its components in the form of a sterilizable system which comprises a filter arrangement which, by means of filter elements dispersed therein, forms an inlet chamber and an outlet chamber, and a receptacle for cellular blood components and a receptacle for blood plasma, where the inlet chamber of the filter arrangement is connected by conduit on the entry side to a blood source and is connected by conduit on the exit side to a receptacle for cellular components of blood, and where the outlet chamber is connected by conduit on the exit side to a receptacle for blood plasma.

A device of this type is disclosed in DE 197 33 407 A1. The device is used, solely by utilizing gravity in a filter arrangement, for fractionating blood into its cellular components with erythrocytes on the one hand and plasma with leukocytes on the other hand, and for collecting in separate receptacles. Devices of this type are used for processing blood in the event of autologous blood donation but also for the processing of blood during blood donation campaigns.

Since the device is connected to human bodies, the device must be sterilized. A method which is frequently used in this connection is steam sterilization. In steam sterilization, moist steam at a temperature of about 120 to 135° C. is guided onto the object to be sterilized. With the known device for fractionating blood into individual ones and/or groups of its components, this leads to various problems. Thus, in the known filter arrangement, on use of steam sterilization and the temperatures associated therewith, a subatmospheric pressure develops in the filter arrangement provided with the filter elements. This leads to the air being sucked out of the connected tubings and the latter collapsing and adhering together. This in turn may impair the later employability and utilizability of the complete device, because the tubings are where appropriate also permanently deformed. In addition, no possibility is provided with the previously disclosed device for being able to pass moist, superheated steam into the assembled system ready for use for the steam sterilization. It is therefore necessary for the individual components to be sterilized inside beforehand separately and apart, or else to dispense with inside sterilization and make do with externally applied steam sterilization or thermal sterilization.

The invention is therefore based on the object of creating a solution which makes it possible to apply thermal sterilization, in particular steam sterilization, comprehensively for sterilizing the device.

With a device of the type defined at the outset, this problem is solved according to the invention by in each case a conduit which is connected to the external environment through a hydrophobic filter, in particular hydrophobic bacterial filter, opening into the conduit on the entry side of the inlet chamber or into the inlet chamber and into the conduit on the exit side of the outlet chamber or into the outlet chamber.

In this connection, the invention likewise provides in an advantageous development for a conduit which is connected to the external environment through a hydrophobic filter, in particular hydrophobic bacterial filter, to open into the conduit on the exit side of the inlet chamber or into the inlet chamber.

Hydrophobic filters, in particular hydrophobic bacterial filters, are water-impermeable filters with a small pore size, for example in the region of 0.2 $\mu$m. Gas, and thus also steam, but no liquid, in particular no water, can pass through these hydrophobic filters. It is thus possible with the aid of these filters in a steam sterilization in the event that a subatmospheric pressure develops in the filter arrangement for air to be sucked in from outside and introduced into the system through the hydrophobic filters, in particular bacterial filters, which are connected by conduit to the filter arrangement. The conduits do not collapse because a continuous pressure equalization takes place. In addition, it is possible to continue the sterilization successfully because the hydrophobic or hydrophilic filters with a pore opening of 0.2 $\mu$m act as bacterial filters, and no bacteria from outside can enter the conduit provided with the respective filter.

However, it is now additionally possible with the aid of the hydrophobic or hydrophilic filters, in particular hydrophobic bacterial filters, for steam to be introduced from outside, through the hydrophobic or hydrophilic filters, into the conduit provided with the respective filter, and thus into the interior of the device, for the thermal sterilization within the framework of the steam sterilization. It is thus possible therefore also for the inside of the device for fractionating blood into its components and/or groups of its components to be exposed and to be sterilized by means of steam sterilization.

Thus, overall, the invention creates the possibility of comprehensive thermal sterilization, in particular by means of steam sterilization, of the complete device, from outside and from inside, after assembling and putting together the individual components which may comprise a filter arrangement, a receptacle for cellular blood components with erythrocytes, a receptacle for blood plasma with leukocytes, but also a leukocyte depletion filter and a blood receptacle, in its entirety. It is thus no longer necessary to sterilize the individual containers and/or components individually. It is possible within the framework of economical fabrication initially to put together the complete configuration of the device which is desired in each case, and then to sterilize it.

The invention provides an embodiment for each hydrophobic or hydrophilic filter, in particular hydrophobic bacterial filter to be associated with a conduit closure element, so that the system is closed after thermal sterilization, in particular steam sterilization, has taken place, and the risk of microbes penetrating in from outside is precluded. After steam sterilization has taken place, the closure elements are closed, so that a device for separating blood into its components is configured as closed system or as system which is closed off toward the external environment.

It is particularly expedient in this connection for the closure element to be disposed in the respective conduit closer to the filter arrangement than to the respective associated hydrophobic or hydrophilic filter, as is likewise provided by the invention.

It is advantageous for fractionating blood into its blood components of plasma and cellular blood components if the flow conditions prevailing at the filter elements of the filter arrangement allow the cellular blood components to flow undamaged along the outside of the filter arrangement. In order to achieve this, the invention further provides for the filter elements of the filter arrangement to be impregnated with a blood-compatible liquid.

However, during the sterilization, this embodiment leads to the problem that this liquid evaporates, escapes from the inlet chamber of the filter arrangement and then condenses and is deposited in the connected conduit which comprises where appropriate a leukocyte removal filter or a leukocyte depletion filter. The condensate would then lead to malfunctioning of the leukocyte depletion filter or lead an unwanted hemolysis, meaning destruction of the blood passed through the leukocyte depletion filter. To prevent this, the invention provides in a development that a closure valve, in particular a disposable rupture valve, is disposed in the conduit on the entry side of the inlet chamber, preferably in the direct vicinity of the filter arrangement.

The filter elements of the filter arrangement are expediently configured as hollow fiber filters with micropores and consist in particular of polyethersulfone or sulfonated polyethersulfone, so that the invention provides for the filter elements to be hollow fiber filters, in particular made of material having micropores, preferably polyethersulfone.

In order to be able to free leukocytes from the blood to be fractionated from leukocytes which are present either in blood or in plasma beforehand, i.e. in the direction of flow in front of the filter arrangement, or else thereafter, i.e. in the direction of flow behind the filter arrangement, the invention further provides for the device to include a leukocyte depletion filter.

It has proved to be particularly advantageous for the leukocyte depletion filter to be disposed in the conduit on the entry side of the inlet chamber of the filter arrangement between the filter arrangement and the blood source and/or the hydrophobic or hydrophilic filter associated with this conduit, as is likewise provided by the invention.

A device which can be employed particularly well is obtained when the device not only can be connected to a blood source, but already comprises one such.

The invention is further distinguished by the device comprising a blood source, and the inlet chamber of the filter arrangement being connected to the blood source.

It is further expedient in this connection for the blood source to comprise a blood receptacle. It is thus possible for example for venous blood initially to be collected and accommodated in a blood, receptacle as collecting container in order then to be fractionated into its components in the filter arrangement. One embodiment of the invention therefore provides for the blood source to comprise a blood receptacle.

In order to obtain a complete device with a compact construction, the invention is then further distinguished by an exit conduit of the blood receptacle being connected by conduit to the conduit on the entry side of the inlet chamber of the filter arrangement. It is then further advantageous in this connection for the device to comprise a blood receptacle provided with a feed conduit and the exit conduit, the feed conduit of which being provided on its end facing away from the receptacle with a connecting element which can be coupled to one or more blood vessels of a donor, as likewise provided by the invention.

Since, as already mentioned at the outset, the invention solves the problem in particular of being able to carry out a steam sterilization comprehensively, the invention is likewise distinguished in a development by the device being steam-sterilizable on the inside by means of steam sterilization by passing steam through the hydrophobic or hydrophilic filters, in particular hydrophobic or hydrophilic bacterial filters. It is possible to pass superheated, moist sterilization steam through the hydrophobic or hydrophilic bacterial filters into the feed conduits and thus into the device, and thus to carry out a steam sterilization also on the insides and inner surfaces of the conduits.

Besides the filter arrangement which may have filter elements impregnated with a blood-compatible liquid, it is also possible for the blood receptacle and the receptacle which accommodates the cellular blood components and erythrocytes to comprise liquids such as a stabilizer for stored blood or a liquid for erythrocyte preservation even at the time of the thermal sterilization, in particular steam sterilization. For a thermal sterilization, in particular steam sterilization, to be possible without problems in this case too, the invention is further distinguished in an advantageous manner by receptacles or filter arrangements which comprise a vaporizable liquid at the time of steam sterilization to include a closure element, in particular a disposable rupture valve, in their connecting conduit to the filter arrangement and/or to the leukocyte filter. This makes it possible to keep the disposable rupture valves closed for example during the steam sterilization, so that no vaporized liquid can escape from the respective receptacles, whereas these valves are opened after sterilization has taken place and to put the device according to the invention into operation, in the case of disposable rupture valves said valves are opened by breaking open, so that a conduit connection now exists between filter arrangement and the respective receiving bag.

Disposable rupture valves are so-called inline valves which are disposed, completely enveloped by the respective tubular feed conduit, which normally consists of synthetic material, in the conduit, so that they are not directly accessible from outside. Such valves consist of telescopic elements which are closed by telescoping the elements, which is possible in the case of flexible plastic tubings by gripping the plastic tubings from outside. These valves are opened by briefly breaking open, which is likewise possible manually by gripping the flexible plastic feed conduits.

For a particularly light and compact embodiment of the complete device to be possible, the invention further provides for the receptacles to be configured in the form of bags and/or bag-like.

In addition, the various units, elements, containers, etc which are combined in the device to give a complete system have dimensions and a spacing apart such that fractionation of blood into its components is possible and takes place solely with the aid of gravity using the complete device. The invention therefore further provides for the receiving bags and the filter arrangement to be disposed at a distance from one another such that the fractionation of blood takes place exclusively through gravity.

Finally, the abovementioned problem is also solved by a method for the steam sterilization of a device, which is distinguished in that sterilization steam is passed into the device through the hydrophobic or hydrophilic filters, in particular hydrophobic or hydrophilic bacterial filters. The configuration of hydrophobic or hydrophilic filters, in particular hydrophobic or hydrophilic bacterial filters, on the tubular conduits leading to or from the filter arrangement, in particular made of plastic tubing, makes it possible for the system or the device also to be sterilized from the inside or on the inside by means of steam sterilization. Further advantages of this method according to the invention correspond to those of the device according to the invention.

BRIEF DESCRIPTION OF THE DRAWINGS

The invention is explained below in more detail by way of example below with reference to the single FIGURE.

The sole FIGURE shows a schematic overall representation of a device for fractionating blood into individual components and/or groups of components in the form of a sterilizable system in accordance with the invention.

DETAILED DESCRIPTION OF PREFERRED EMBODIMENTS

The single FIGURE shows in a diagrammatic overall representation the device, designated 1 overall, for fractionating blood into individual ones and/or groups of its components in the form of a sterilizable system. The device comprises a filter arrangement 2 which forms, by means of filter elements 3 dispersed therein, an inlet chamber 4 and an outlet chamber 5. The device 1 further comprises a receptacle 6 to receive cellular blood components which are removed in the filter arrangement 2 and which comprise erythrocytes, and a receptacle 7 for blood plasma which is removed in the filter arrangement 2 and comprises the leukocytes. The inlet chamber 4 of the filter arrangement 2 is connected by conduit on the exit side by means of a conduit 8 which is configured as plastic tubing and consists of the conduit segments 8a and 8b to the receptacle 6 for cellular components of blood. The outlet chamber 5 of the filter arrangement 2 is connected by conduit on the exit side by means of a conduit 9 formed from a plastic tubing to the receptacle 7 for blood plasma.

The device 1 further comprises a blood source which is designated overall by 10 and comprises a blood receptacle 11 and a puncture needle 12 which is connected via a conduit 13 to the blood receptacle 11. It is thus possible for venous or arterial blood to be collected in the blood receptacle 11 and be provided as blood source. However, it is also possible at this point to provide only blood which is derived from a blood donation and is present in a bag-like receptacle 11 as blood source 10. The blood receptacle 11 is connected on the exit side by means of a conduit 14 which comprises conduit segments 14a and 14b and is formed from a plastic tubing to the entry side of the inlet chamber 4 of the filter arrangement 2.

The receptacles 6, 7 and 11 are configured in the form of bags or bag-like and, like known blood transfusion bags, are flexible in relation to their stability. Before the blood fractionation is carried out, and also before a sterilization of the complete system or of the complete device 1 is carried out, a vaporizable liquid for erythrocyte preservation (mannitol) is present in the receiving bag 6, and a liquid, likewise vaporizable stabilizer for stored blood is present in the receiving bag 11. The hollow fiber filters 15 which form micropores and consist in particular of polyethersulfone are likewise impregnated with a blood-compatible liquid.

A conduit 17 which is formed by a plastic tubing opens into the conduit 14 on the entry side of the inlet chamber 4 by means of a three-ended connecting element 16a and is connected on its side facing away from the three-ended connecting element 16a via a hydrophobic or hydrophilic bacterial filter 18 to the external environment. A conduit closure element 19 is formed in the conduit 17 between the hydrophobic or hydrophilic bacterial filter 18 and the three-ended connecting element 16a.

A conduit 20 which is formed by a plastic tubing and which has at its end facing away from the outlet chamber 5 a hydrophobic or hydrophilic bacterial filter 21, via which the conduit 20 is connected to the external environment, likewise opens into the outlet chamber 5 of the filter arrangement 2. In addition, the conduit 21 also has a conduit closure element 22. A conduit 23 also opens into the conduit 8 on the exit side of the inlet chamber 4 of the filter arrangement 2 by means of a three-ended connecting element 16b and is provided on its end facing away from the three-ended connecting element 16b with a further hydrophobic or hydrophilic bacterial filter 24 and is connected via this hydrophobic or hydrophilic bacterial filter 24 to the external environment. A conduit closure element 25 is formed in the conduit 23 between the hydrophobic or hydrophilic bacterial filter 24 and the three-ended connecting element 16b.

A valve, in particular a disposable rupture valve 26, 27, which is located inside the tubing conduit 14 is disposed in the conduit 14 both in its end region in the region of the blood receptacle 11 and in its end region in the region of the inlet chamber 4 of the filter arrangement 2 in each case. A further valve 28, in particular also a disposable rupture valve in this case, is disposed in the conduit 8 in the vicinity of its end in the region of the receptacle 6, likewise located inside the tubing conduit 8.

A leukocyte separating filter or a leukocyte depletion filter 29 is disposed in the conduit 14 between blood receptacle 11 and the filter arrangement 2 and also between the filter arrangement 2 and the three-ended connecting element 16a and thus the opening of the conduit 17 into the conduit 14. The conduit 14 further comprises an adjusting element 30 with the aid of which the flow rate of the liquid flowing in the conduit 14 to the filter arrangement 2 can be controlled. A conduit closure element 31 is additionally disposed in the conduit 9 leading to the receptacle 7 and, finally, the receptacle 6 includes on the exit side a conduit 33 closed with a stopper 32.

It is possible with the aid of the device 1, solely through gravity, for blood taken from the blood receptacle 11 to be fractionated in the filter arrangement 2 into blood plasma with leukocytes, which is then collected via the outlet chamber 5 of the filter arrangement 2 in the receptacle 7, and to be fractionated into cellular blood components with erythrocytes, which are then collected via the conduit connection 8 on the exit side of the inlet chamber 4 in the receptacle 6. A device of this type must be sterilized before being put into operation and used on the human body. For this device 1 to be sterilizable, it is provided with hydrophobic or hydrophilic bacterial filters 18, 21 and 24, each of which are connected by conduits to the inlet chamber 4 and/or the outlet chamber 5 of the filter arrangement 2 in such a way that all entry and exit sides and thus the entire internal region of the filter arrangement 2, but also the conduits 8, 9 and 14 which are connected to the respective entry and/or exit side of the filter arrangement 2, and the receptacles 6, 7 and 11 which are each connected to the end, facing away from the filter arrangement 2, of these conduits 8, 9 and 14, are reached or can be reached by the superheated, moist sterilization steam introduced through the hydrophobic or hydrophilic bacterial filters into the connected conduits. It is thus possible with this configuration to sterilize the entire inner walls and inner surfaces of the device 1 with the aid of steam sterilization. After a steam sterilization has taken place, the conduits 17, 20 and 23 including the hydrophobic or hydrophilic bacterial filters can be closed by means of the conduit closure elements 19, 22 and 25 disposed therein, so that it is subsequently impossible for any environmental air to penetrate into the system through these conduits.

It is additionally possible, before carrying out a steam sterilization which acts from outside on the elements and components, and devices and units of the device 1, to close the valves 26, 27 and 28 which are located in the conduits 14 and 8 directly on the receptacles 6 and 11 connected thereto, and on the filter arrangement 2, so that liquid present in the receptacles 6 and 11, and in the filter arrangement 2, cannot escape from the receptacles 6, 11 and the filter arrangement 2 into the connected conduits and condense there.

A steam sterilization can be carried out for example in such a way that firstly the closure elements 19, 22, 25 and 31, and the valves, in particular disposable rupture valves 26, 27 and 28, are opened, and a steam sterilization takes place both from outside on the device 1 and by passing sterilization steam through the hydrophobic or hydrophilic bacterial filters 18, 21 and 24 into the connected conduits 17, 20 and 23. After a sufficiently long sterilization time, the valves, in particular disposable rupture valves 26, 27 and 28, are then closed, so that liquid present in the containers 6, 11 and the filter arrangement 2 can no longer escape and evaporate.

In cases where it is not ensured, through the simultaneous entry of sterilization steam into the system, that liquid present in the containers 6, 11 and the filter arrangement 2 cannot evaporate and escape, the valves 26, 27 and 28 are closed before starting the sterilization method. Sterilization of the containers 6 and 11 then takes place solely through steam sterilization acting on the containers from outside.

The other conduit regions are also sterilized from inside by the sterilization steam which can be passed in through the hydrophobic or hydrophilic filters 18, 21 and 24.

However, even if only a steam sterilization which acts from outside on the device is intended, an advantageous steam sterilization takes place through initially closing the disposable rupture valves 26, 27 and 28 and then carrying out the steam sterilization, meaning the exposure of the system to superheated, moist sterilization steam in the temperature range from 120 to 135° C. The complete device is sufficiently sterilized by this sterilization. Any liquid present in the containers 6 and 11 cannot escape therefrom since the valves 26 and 28 are closed. It is likewise impossible for liquid or vaporized liquid to escape from the filter arrangement 2 into the conduit 14. Collapse of the conduits 14, 8 and 20, and 9, is prevented by carrying out the sterilization with opened closures 19, 22 and 25 and, where appropriate, 31, so that the corresponding conduits are able to suck air into the conduits through the hydrophobic or hydrophilic bacterial filters 18, 21 and 24 from the external environment as soon as a subatmospheric pressure is set up in the filter arrangement 2.

After the sterilization has been carried out, the closure elements 19, 22 and 25 are closed. If it is then intended to carry out the blood separation process, the disposable rupture valves 26, 27 and 28 are opened by breaking open so that blood now escape from the blood receptacle 11 into the conduit 14 and, after passing through the leukocyte depletion filter 29, enter the inlet chamber 4 and be fractionated by means of the filter elements 3 into the cellular blood components which are collected in receptacle 6 and into the plasma components which are collected in receptacle 7. In this case, the cellular blood components remain on the side of the filter elements facing the inlet chamber, whereas the blood plasma pass through the pores of the filter elements onto the side of the filter elements facing the outlet chamber.

When the blood receiving bag 11 is emptied, the closure 19 is then opened again, so that a pressure equalization can take place in the leukocyte depletion filter, which also allows final residues of blood present in the leukocyte depletion filter 29 to escape into the filter arrangement 2.

Should an air bubble have formed in the erythrocyte bag 6 at the end of the blood separation process, this air bubble can be blown out by appropriate impact on the bag 6 through the hydrophobic or hydrophilic filter 24, for which purpose the conduit closure element 25 is opened once again.

The filter elements 3 are hollow fiber filters which are known from membrane filtration, in particular ultrafiltration. An example thereof is a hollow fiber filter which comprises or consists of membranes with PES-TF 10 (supplied by Akzo) microfibers made of polyethersulfone/sulfonated polyethersulfone material. The membranes have an average internal diameter of 300 µm, an average wall thickness of 100 µm and a maximum pore size of 0.5 µm. The hollow fiber filters are disposed as tubular single elements side by side in such a way that the entirety of the inner regions of the hollow fibers forms the inlet chamber 4 and the entirety of the outer regions of the hollow fibers forms the outlet chambers 5. After the steam sterilization or thermal sterilization has been carried out, the conduits disposed on the inlet chamber 4 and the outlet chamber 5 of the filter arrangement 2 are all connected air-tight and microbe-tight to the receptacles 6 for cellular blood components and 7 for blood plasma, and the blood receptacle 11.

The invention claimed is:

1. A device for fractionating blood comprising
a filter arrangement which, forms an inlet chamber and an outlet chamber, and
a receptacle for cellular blood components and a receptacle for blood plasma,
the inlet chamber of the filter arrangement having (i) an inlet chamber entry side connected by a first conduit to a blood source and (ii) an inlet chamber exit side connected via a second conduit to the receptacle for cellular components of the blood,
wherein blood enters the inlet chamber, passes through the filter element to separate the blood plasma from the blood, and exits into the second conduit, the blood plasma so separated being collected in the outlet chamber for separate removal, the outlet chamber having an outlet chamber exit side connected by a third conduit to the receptacle for blood plasma,
wherein said system is sterilizable with superheated moist steam,
said first and second conduits are connected to a first and second connected conduit, respectively,
said outlet chamber is connected to a third connected conduit,
said first, second, and third connected conduits comprise a first, second, and third terminating, porous, liquid-impermeable bacterial filter, respectively, allowing the superheated moist steam to be moved through the device via said bacterial filters, and
said first, second, and third conduits, and said connected conduits comprise flexible plastic tubing.

2. The device as claimed in claim 1, wherein each terminating hydrophobic bacterial filter is associated with a conduit closure element.

3. The device as claimed in claim 2, wherein the conduit closure element is disposed in the respective connected conduit closer to the filter arrangement than to the respective associated terminating hydrophobic bacterial filter.

4. The device as claimed in claim 1, wherein the filter element is impregnated with a blood-compatible liquid.

5. The device as claimed in claim 1, wherein a disposable rupture closure valve is disposed in the first conduit on the inlet chamber entry side.

6. The device as claimed in claim 1, wherein the filter element is a hollow fiber filer made of material having micropores.

7. The device as claimed in claim 1, wherein the device further comprises a leukocyte depletion filter.

8. The device as claimed in claim 7,
wherein a first terminating hydrophobic bacterial filter of the terminating hydrophobic bacterial filters is associated with the first conduit, and
wherein the leukocyte depletion filter is disposed in the first conduit.

9. The device as claimed in claim 1, wherein the blood source comprises a blood receptacle.

10. The device as claimed in claim 9, wherein an exit conduit of the blood receptacle is connected by a fourth conduit to the first conduit on the inlet chamber entry side.

11. The device as claimed in claim 9, wherein the blood receptacle is connected with a blood feed conduit and the first conduit, the blood feed conduit being provided at an end of the blood feed conduit with a connecting element which can be coupled to one or more blood vessels of a donor.

12. The device as claimed in claim 7, wherein the receptacle for cellular blood components or the filter arrangement which comprise a vaporizable liquid at the time of steam sterilization include a disposable rupture closure valve, in their respective connecting conduit to the filter arrangement and/or to the leukocyte depletion filter.

13. The device as claimed in claim 1, wherein the receptacles comprise receiving bags.

14. The device as claimed in claim 13, wherein the receiving bags and the filter arrangement are disposed at a distance from one another such that the fractionation of blood takes place exclusively through gravity.

15. A method for steam sterilization comprising:
assembling a device for fractionating blood into single components and/or groups of its components comprising a filter arrangement which, via a filter element disposed therein, forms an inlet chamber and an outlet chamber, and a receptacle for cellular blood components and a receptacle for blood plasma, by connecting an inlet chamber entry side of the inlet chamber of the filter arrangement by a first conduit to a blood source and an inlet chamber exit side of the inlet chamber via a second conduit to the receptacle for cellular components of the blood,
wherein blood enters the inlet chamber, passes through the filter element to separate the blood plasma from the blood, and exits into the second conduit, the blood plasma so separated being collected in the outlet chamber for separate removal, and
connecting an outlet chamber exit side of the outlet chamber by a third conduit to the receptacle for blood plasma,
wherein said first and second conduits are connected to a first and second connected conduit, respectively,
said outlet chamber is connected to a third connected conduit,
said first, second, and third connected conduits comprise a first, second, and third terminating, porous, liquid-impermeable bacterial filter, respectively, allowing the superheated moist steam to be moved through the device via said bacterial filters, and
said first, second, and third conduits, and said connected conduits comprise flexible plastic tubing, and
passing superheated moist sterilization steam through the bacterial filters into the device.

16. The device for fractionating blood according to claim 1, wherein the filter element is U-shaped.

* * * * *